United States Patent
Petersen

(10) Patent No.: US 6,555,392 B1
(45) Date of Patent: Apr. 29, 2003

(54) ANTISERA TRAY

(75) Inventor: Eric Petersen, Beaumont, TX (US)

(73) Assignee: Helena Laboratories Corporation, Beaumont, TX (US)

( * ) Notice: Subject to any disclaimer, the term of this patent is extended or adjusted under 35 U.S.C. 154(b) by 0 days.

(21) Appl. No.: 09/394,038

(22) Filed: Sep. 13, 1999

(51) Int. Cl.[7] .................................. G01N 33/538
(52) U.S. Cl. ................ 436/541; 436/538; 422/68.1; 422/99; 422/102; 422/104; 204/456; 204/465; 204/193; 204/194; 204/403; 435/4; 435/5; 435/6; 435/7.1
(58) Field of Search ................. 422/68.1, 99, 102, 422/104; 204/456, 465, 193, 194, 403; 435/4, 5, 6, 7.1; 436/541, 538

(56) References Cited

U.S. PATENT DOCUMENTS

| | | | | |
|---|---|---|---|---|
| 3,802,844 A | * | 4/1974 | Sendra et al. ................. 23/259 |
| 3,844,918 A | * | 10/1974 | Cawley ....................... 204/180 |
| 3,858,835 A | * | 1/1975 | Baren ........................ 248/94 |
| 4,060,457 A | * | 11/1977 | Iizuka et al. ................. 195/127 |
| 4,061,561 A | * | 12/1977 | Fletcher et al. ............. 204/299 |
| 4,111,785 A | * | 9/1978 | Roskam ....................... 204/299 |
| 4,188,986 A | * | 2/1980 | Wetterlin et al. ........... 141/130 |
| 4,407,958 A | * | 10/1983 | DeGraff, Jr. ................. 435/287 |
| 4,411,868 A | * | 10/1983 | Noack ........................ 422/104 |
| 4,438,068 A | * | 3/1984 | Forrest ....................... 422/61 |
| 4,599,315 A | * | 7/1986 | Terasaki et al. ............. 435/301 |
| 4,668,363 A | * | 5/1987 | Gebott et al. ............. 204/182.8 |
| 4,682,890 A | * | 7/1987 | De Macario et al. ....... 356/244 |
| 4,741,814 A | * | 5/1988 | Mayes et al. ................ 204/299 |
| 4,770,856 A | * | 9/1988 | Uthemann et al. .......... 422/104 |
| 4,882,127 A | * | 11/1989 | Rosenthal et al. ............. 422/50 |
| 5,041,266 A | * | 8/1991 | Fox ............................ 422/102 |
| 5,112,470 A | * | 5/1992 | Sylvester ..................... 204/299 |
| 5,137,614 A | * | 8/1992 | Golias ........................ 204/199 |
| 5,213,766 A | * | 5/1993 | Flesher et al. .............. 422/102 |
| 5,238,651 A | * | 8/1993 | Chuba ........................ 422/104 |
| 5,284,565 A | * | 2/1994 | Chu et al. .................... 204/299 |
| 5,337,894 A | * | 8/1994 | Ivey .......................... 206/370 |
| 5,406,456 A | * | 4/1995 | Hsu ........................... 361/796 |
| 5,489,532 A | * | 2/1996 | Charm et al. ............. 435/286.1 |
| 5,512,157 A | * | 4/1996 | Guadagno et al. .......... 204/616 |
| 5,571,481 A | * | 11/1996 | Powell et al. ............... 422/104 |
| 5,598,933 A | * | 2/1997 | Lessard et al. ............... 211/74 |
| 5,620,663 A | * | 4/1997 | Aysta et al. ................. 422/104 |
| 5,632,388 A | * | 5/1997 | Morrison et al. ............. 211/74 |
| 5,665,558 A | * | 9/1997 | Frame et al. .............. 435/7.25 |
| 5,772,966 A | * | 6/1998 | Maracas et al. ............ 422/100 |
| 5,843,295 A | * | 12/1998 | Steiner et al. .............. 204/619 |
| 5,935,524 A | * | 8/1999 | Bass et al. .................. 422/104 |
| 5,948,691 A | * | 9/1999 | Ekiriwang et al. .......... 436/183 |
| 5,950,832 A | * | 9/1999 | Perlman ..................... 206/446 |
| 5,968,331 A | * | 10/1999 | Kambara et al. ........... 204/450 |
| 6,001,310 A | * | 12/1999 | Shaffer et al. .............. 422/102 |
| 6,132,684 A | * | 10/2000 | Marino ....................... 422/104 |
| 6,165,541 A | * | 12/2000 | Merchant et al. .......... 427/2.11 |
| 6,241,949 B1 | * | 6/2001 | Kane ......................... 422/102 |

* cited by examiner

Primary Examiner—Christopher L. Chin
Assistant Examiner—Pensee T. Do
(74) Attorney, Agent, or Firm—Piper Rudnick LLP; Jerold I. Schneider

(57) ABSTRACT

An improvement in the immunofixation electrophoresis procedure for detecting proteins in serum, urine or cerebral spinal fluids. Multiple samples from a single patient are placed on a gel and subjected to electrophoresis for resolving or separating proteins. A container has multiple receptacles which store, separately, various antisera. The separate antisera are withdrawn from the receptacles and simultaneously applied to the sample areas for subsequent incubation. The receptacles are preferably arranged in multiple series in the container, each series offset from, and partially overlapping, the receptacles of the next series.

17 Claims, 2 Drawing Sheets

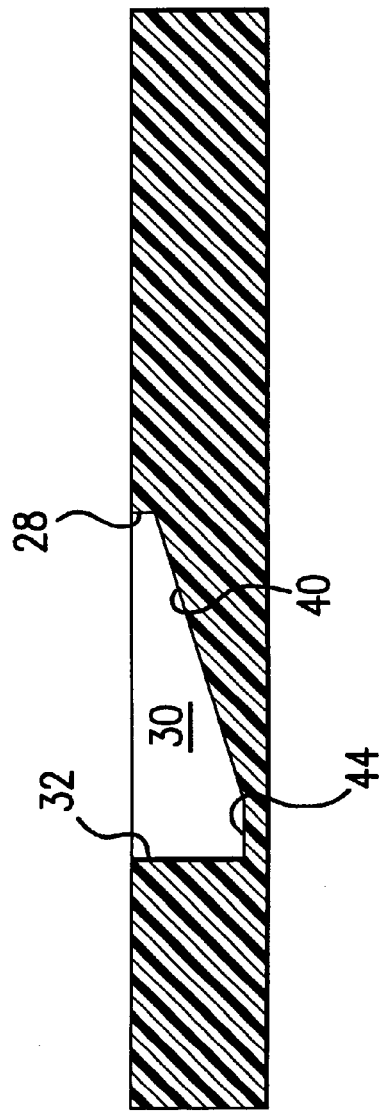
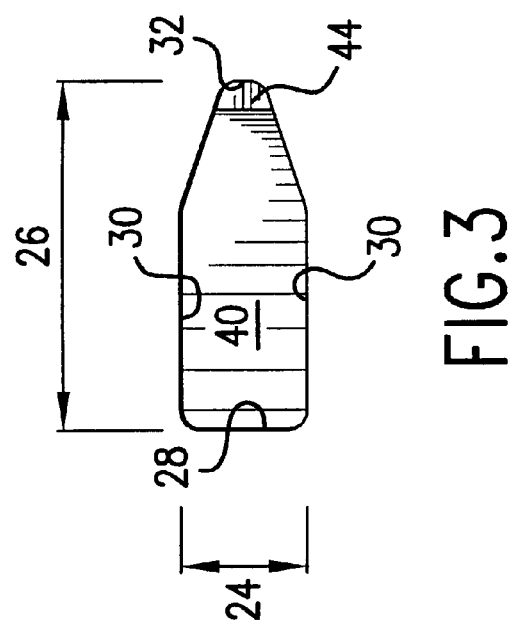

ANTISERA TRAY

BACKGROUND ART

This invention relates to a container for storing multiple, discrete chemicals for subsequent dispensing and has particular utility as an antisera container or tray for use in an immunofixation electrophoresis system.

Immunofixation electrophoresis, referred to as IFE, is well-known as a two-stage procedure for detecting the presence of certain proteins in human serum, urine or cerebral spinal fluid. The procedure involves, as a first step, protein fraction resolution by electrophoresis. As a second step, the soluble antigen in each protein fraction is allowed to react with its antibody. The resultant antigen-antibody complexes will precipitate, at a rate dependent upon the proportion of the reactants, temperature, salt concentration and pH. The antigen-antibody complexes are then visualized by staining.

The IFE process is described in greater detail in Gebott et al, U.S. Pat. No. 4,668,363 issued May 26, 1987, which is hereby incorporated by reference. Apparatus and chemicals for performing IFE have been marketed for some time by Helena Laboratories Corporation of Beaumont, Tex.

Typically, a specimen from a single patient is diluted and then placed in multiple sample or application areas (also referred to as zones or channels) on a single electrophoretic gel plate. The purpose of utilizing multiple sample areas is to enable detection separately of total serum protein, and various proteins such as the immunoglobin heavy chains IgG, IgM, IgA and light chains Kappa and Lambda, or other proteins whose presence or absence may be of importance in medical diagnosis. As known in the prior art, various antisera (i.e., fluid containing the antibody) such as IgG, IgM, etc., are deposited on the appropriate zones and permitted to react with the antigen in the sample. The term "incubation" refers to the time interval during which the antisera and antibody are in contact such that a reaction may occur.

U.S. Pat. No. 5,137,614, issued on Aug. 11, 1992 to Golias, which is hereby incorporated by reference, is directed to a control system for verifying the effectiveness of the chemicals utilized in the immunofixation electrophoresis procedure. This is accomplished without the need to interrupt patient specimen evaluation when chemicals are replenished, since the chemical utilized on the specimens are also utilized in the control test. The control system verifies that the chemicals have retained their lability.

U.S. Pat. No. 3,844,918, issued on Oct. 29, 1974 to Crawley, which is hereby incorporated by reference, is directed to a template which includes an aperture through which serum is received. The template is placed on a mold having an extended portion which passes through the aperture. Gel is coated on one surface of the template. When the gel molds around the portion extending through the aperture, the mold is removed from the template. The template is left with a small cavity in which the serum is placed.

U.S. Pat. No. 5,403,456, issued on Apr. 4, 1995 to Bellon, which is hereby incorporated by reference, is directed to a mask which includes an orifice through which liquid is deposited on the zone of the gel, and a slit through which excess liquid is withdrawn from the zone of the gel after the incubation step. In practice, the mask is placed in close proximity to, but spaced apart from the surface of the gel, the liquid is deposited through the mask onto the gel, the mask is maintained in its relative position during the incubation step, and, thereafter, excess liquid is withdrawn through the mask. Then, of course, the mask, is removed.

It is preferred, for reasons of economy, to evaluate multiple samples (e.g., of multiple patients) simultaneously. This has been accomplished, in the past, using multiple zones on a single electrophoresis gel. Thus if six zones are required for a single patient, if the samples from six patients are to be evaluated simultaneously, then 6×6 or 36 zones or channels are used on the electrophoresis gel. Then, after the electrophoresis step, the appropriate antisera must be applied to the corresponding zone for each patient. For example, if blood samples of six patients are being evaluated simultaneously, then after the electrophoresis step, one antisera (e.g., IgG antisera) was applied sequentially to the corresponding zone for each patient using a pipette of the type which has a removable, disposable tip. Then, the tip on the pipette would be removed, and another antisera (e.g., IgM antisera) would be applied sequentially to the corresponding zone for each patient using a second disposable tip. This procedure would be repeated for each of the antisera. Of course it was possible to apply the various antisera to the corresponding zones for a single patient, and then repeat the process for the next patient, etc., but this would be cumbersome, time consuming, and create a potential for errors because of the large number of pipette tips which would be used, i.e., 36 tips in the above example.

Applicant has discovered that while multiple sample pipettes have existed for some time, prior to the present invention those multiple sample pipettes could not be used to simultaneously apply antisera to the corresponding zones for a single patient. To the contrary, notwithstanding that multiple sample pipettes were well known, single sample pipettes were used, and the replacement tips were changed before each "different" antisera.

SUMMARY OF INVENTION

The present invention overcomes the difficulties and shortcomings of the prior art by providing a container or tray, for holding and maintaining separate, multiple discrete chemicals such that a multiple sample pipette system can be used to simultaneously apply the antisera to all the zones for a single patient, thus increasing the accuracy and usability of an electrophoresis plate which permitted samples from multiple patients from being processed simultaneously.

BRIEF DESCRIPTION OF DRAWINGS

The various objects, advantages and benefits of the present invention will become more apparent upon reading the following detailed description of the invention taken in conjunction with the drawings. In the drawings:

FIG. 2 is a cross-section view of a portion of the tray of FIG. 1 as seen in the direction of arrows 2—2 of FIG. 1; and FIG. 3 is a plan view of a single receptacle of the antisera tray of FIG. 1.

DESCRIPTION OF THE INVENTION

Figure 1:
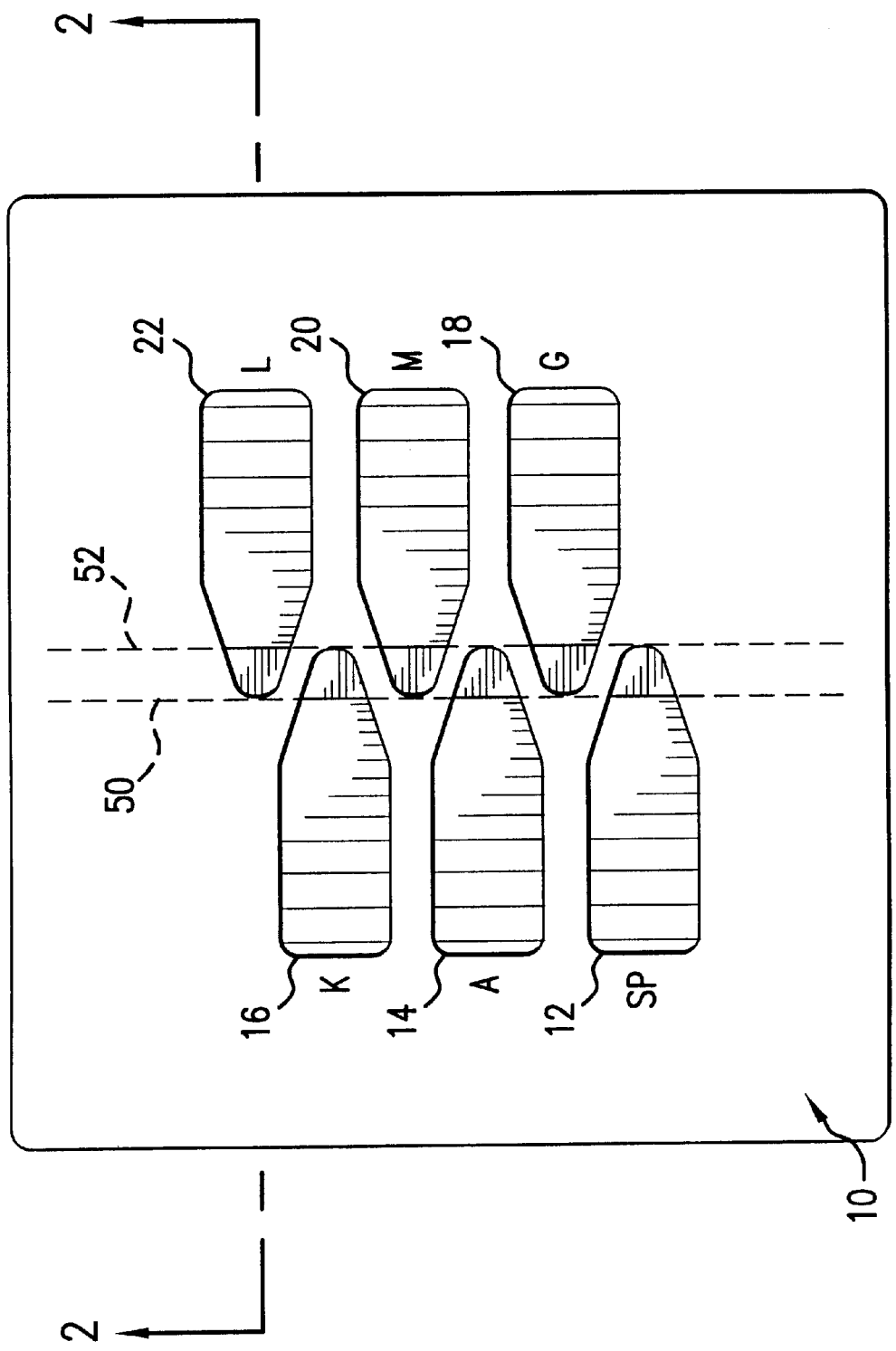
FIG. 1 is a plan view of a container or antisera tray according to the present invention.

In the broader sense, the present invention is a receptacle for separately storing/maintaining a plurality of chemicals for subsequent dispensing and preferably simultaneous dispensing. The present invention is, for convenience, described in the non-limiting but merely illustrative context of an antisera tray for use in immunofixation electrophoresis.

With reference to the drawings, an antisera tray 10 which may be formed of plastic and includes six generally elongated receptacles 12, 14, 16, 18, 20 and 22. The receptacles 12, 14 and 16 are spaced apart and arranged in a first set or series and, in the illustrated example would contain the antisera for SP, IgA, and IgK, respectively. The receptacles 18, 20, and 22 are spaced apart and arranged in a second set or series which is spaced apart from, and offset relative to, the receptacles in the first series, and, in the illustrated example, would contain the antisera for IgG, IgM and IgL, respectively.

The receptacles are essentially the same, and a receptacle will be described in detail with reference to both FIG. 2 and FIG. 3. As seen most easily in plan view, a receptacle has a width 24 and a length 26, a rear wall 28 and side walls 30. The side walls are parallel to each other and thereafter taper toward each other and away from the rear wall 28 to culminate in a slightly rounded nose portion 32.

As seen most easily in the cross-sectional view of FIG. 2, the receptacle has a floor 40 which tapers downwardly from the rear wall 28 toward the nose 32. The taper of the floor terminates adjacent the nose such that a portion 44 of the floor is flat.

Referring back to FIG. 1, it may be appreciated that the nose 32 of each receptacle in the first series is positioned intermediate the nose 32 of the receptacles in the second series, and the first and second series, although offset, do include a degree of overlap. In FIG. 1, two imaginary lines 50, 52 are superimposed on the tray in a direction perpendicular to the longitudinal axis of the receptacles, approximately where the taper of each floor terminates. Hence the portion of each receptacle between the lines 50, 52 has a flat floor, and this defines the degree of overlap among the six receptacles. It should be appreciated, however, that the foregoing is for the purpose of explanation and not intended as a limitation, since the degree of overlap among the receptacles is not restricted to the portion of the receptacles where the floor is flat. The overlap permits simultaneous insertion, into various receptacles, of the disposable tips of a multiple sample pipette as will now be explained.

In use, the six receptacles are filled, each with an appropriate antisera. Then, a multiple sample pipette, with multiple, disposable tips, is inserted into the antisera tray, such that each disposable tip is inserted into a corresponding receptacle simultaneously. After the pipette tips are filled, the pipette is moved to the electrophoresis gel (the samples have already been electrophoresed) and the six antisera are simultaneously dispensed (or applied) on the six channels or zones for a single patient. The multiple sample pipette is then returned to the tray, the tips are again filled, and the pipette moved to the electrophoresis gel, and the six antisera are thereafter simultaneously dispensed on the six channels or zones for the next patient. The process is repeated until the antisera have been applied to all zones for all patients, and thereafter the immunofixation electrophoresis continues with the incubation step. One form of multiple sample pipette which has been used successfully is the Finnpipette Digital, Catalog No. 1116, manufactured by Labsystems, which is located in Finland.

Although not illustrated, the application of the antisera onto the zones of the electrophoresed samples is through a template of the type marketed by Helena Laboratories Corporation of Beaumont, Tex.

It should be appreciated that, in the foregoing example, if samples from less than six patients (e.g., four patients) are to be processed simultaneously, then the multiple channel pipette can still be used, because all six antisera are simultaneously deposited on all six zones corresponding to the samples from a single patient. Thus the pipette is "reloaded" and antisera dispensed four times if there are samples from only four patients.

Many other changes and modifications may be made without departing from the spirit and scope of the present invention. The present invention, therefore, should be limited only by the following claims.

What is claimed is:

1. A system for immunofixation electrophoresis, comprising:
    a tray for storing and separately maintaining a plurality of chemicals, the tray including:
        a plurality of receptacles arranged in at least two series, the at least two series including a first series and a second series, wherein each receptacle has a floor, and at least part of the floor in each receptacle in the first series is tapered toward the second series;
    the receptacles in each series being spaced apart from the receptacles in the other series;
        each receptacle having an interior portion and an opening for access to said interior portion;
        the receptacles in said first series being offset from, and partially overlapping, the receptacles in said second series; and
        the openings of the receptacles being aligned for simultaneous access to the interior portions of the receptacles; and
    a delivery device for delivering a sample to at least one receptacle.

2. The system of claim 1, wherein the chemicals are antisera.

3. The system of claim 1, wherein at least part of the floor in each receptacle in the second series is tapered toward the first series.

4. The system of claim 1, wherein at least a part of the floor in each receptacle in the first series is sloped relative to the second series.

5. The system of claim 1, wherein each receptacle has a floor, and at least a part of the floor in each receptacle in the first series is sloped relative to the second series.

6. The system of claim 1, wherein the delivery device is a pipette.

7. The system of claim 6, wherein the delivery device is for delivering a plurality of samples to the plurality of receptacles.

8. The system of claim 1, wherein each receptacle has a tapered end.

9. A system for immunofixation electrophoresis, comprising:
    a tray having formed therein a plurality of receptacles; and
    a delivery device capable of delivering a sample to at least one of the receptacles;
    wherein each of the receptacles has an opening and a floor, the floor being including a sloped portion;
    wherein the plurality of receptacles form a first row and a second row;
    wherein at least a portion of the openings of all of the plurality of receptacles are in overlapping alignment; and
    wherein the opening of each of the receptacles has a tapered end.

10. The system of claim 9, wherein the delivery device is a pipette for delivering a plurality of samples to a plurality of receptacles simultaneously.

11. The system of claim 9, wherein the sample includes antisera.

12. The system of claim 9, wherein at least part of the opening of each receptacle in the first row is tapered toward the second row.

13. The system of claim 12, wherein at least part of the opening of each receptacle in the second row is tapered toward the first row.

14. The system of claim 9, wherein at least part of the floor in each receptacle in the first series is sloped relative to the second series.

15. The system of claim 9, wherein at least part of the floor in each receptacle in the second series is sloped relative to the first series.

16. The system of claim 9, wherein the delivery device is a pipette.

17. The system of claim 9, wherein the delivery device is for delivering a plurality of samples to the plurality of receptacles.

* * * * *